(12) United States Patent
MacLean

(10) Patent No.: US 11,963,925 B2
(45) Date of Patent: Apr. 23, 2024

(54) BIRTHING POOL MONITOR SYSTEM AND METHOD

(71) Applicant: The Good Birth Company Limited, Birmingham (GB)

(72) Inventor: Adam MacLean, Birmingham (GB)

(73) Assignee: The Good Birth Company Limited, Birmingham (GB)

( * ) Notice: Subject to any disclaimer, the term of this patent is extended or adjusted under 35 U.S.C. 154(b) by 362 days.

(21) Appl. No.: 17/424,688

(22) PCT Filed: Jan. 21, 2020

(86) PCT No.: PCT/GB2020/050131
§ 371 (c)(1),
(2) Date: Jul. 21, 2021

(87) PCT Pub. No.: WO2020/152456
PCT Pub. Date: Jul. 30, 2020

(65) Prior Publication Data
US 2022/0104999 A1  Apr. 7, 2022

(30) Foreign Application Priority Data

Jan. 22, 2019 (GB) .................................... 1900882

(51) Int. Cl.
*A61H 33/00* (2006.01)
*A61B 8/08* (2006.01)
(Continued)

(52) U.S. Cl.
CPC ....... *A61H 33/005* (2013.01); *A61G 13/0009* (2013.01); *E04H 4/0025* (2013.01);
(Continued)

(58) Field of Classification Search
CPC .......... A61H 33/005; A61H 2201/0103; A61H 2201/5092; A61H 2230/625;
(Continued)

(56) References Cited

U.S. PATENT DOCUMENTS 9,427,115 B2* 8/2016 Jechart ................. G08B 21/084
11,118,365 B2* 9/2021 Segal ........................ B63C 9/02
(Continued)

FOREIGN PATENT DOCUMENTS

EP    1138305 A1   4/2001
GB    2432116 A    5/2007
(Continued)

OTHER PUBLICATIONS

Kr 20030067888A English machine translation printed Sep. 13, 2023 (Year: 023).*
(Continued)

*Primary Examiner* — Christine J Skubinna
(74) *Attorney, Agent, or Firm* — Caesar Rivise, PC

(57) ABSTRACT

A system (2; 4) for measuring the movement of a birthing mother in a birthing pool (1; 3), the system comprises: a) a birthing pool (1; 3), the pool (1; 3) comprising a base (11; 31) and a peripheral wall (12; 32) upstanding from the base (11; 31), the pool (1; 3) further comprising at least one motion sensor (21, 22; 41, 42), the motion sensor (21, 22; 41, 42) being located adjacent the peripheral wall (12; 32) and/or on the base (11; 31), and wherein the at least one motion sensor (21, 22; 41, 42) is configured or configurable to detect the movement of the birthing mother in the pool (1; 3); b) a processing means, e.g. a processor, operatively connected to the at least one motion sensor (21, 22; 41, 42); wherein the system is configured to monitor motion of the mother whilst located within the birthing pool (1; 3).

20 Claims, 4 Drawing Sheets

(51) Int. Cl.
*A61G 13/00* (2006.01)
*E04H 4/00* (2006.01)
*G08B 21/02* (2006.01)
*G16H 40/63* (2018.01)

(52) U.S. Cl.
CPC .......... *E04H 4/0037* (2013.01); *G08B 21/02* (2013.01); *G16H 40/63* (2018.01); *A61B 8/0866* (2013.01); *A61H 2201/0103* (2013.01); *A61H 2201/5092* (2013.01); *A61H 2230/625* (2013.01)

(58) Field of Classification Search
CPC .............. A61G 13/0009; E04H 4/0025; E04H 4/0037; G08B 21/02; G16H 40/63; A61B 8/0866; A61B 5/11; A61B 5/6887; A61B 5/4343; A61B 5/1114; A61B 5/1116; A61B 8/00
See application file for complete search history.

(56) References Cited

U.S. PATENT DOCUMENTS

| | | | |
|---|---|---|---|
| 11,322,010 B1* | 5/2022 | Madden | G08B 21/086 |
| 2009/0178191 A1* | 7/2009 | MacLean | A61G 13/0009 4/506 |
| 2019/0117199 A1* | 4/2019 | Schmitt | A61B 8/4477 |

FOREIGN PATENT DOCUMENTS

| | | | |
|---|---|---|---|
| KR | 20000030762 | | 6/2000 |
| KR | 20030067888 A | * | 8/2003 |
| KR | 20030067888 A | | 8/2003 |

OTHER PUBLICATIONS

International Search Report for PCT/GB2020/050131 dated May 4, 2020.
Written Opinion for PCT/GB2020/050131.
English-language Abstract of KR 20030067888.
Abstract of KR20000030762.
Cluett et al., "Immersion in water in pregnancy, labour and birth", Cochran Database of Systematic Reviews, Issue 2, No. CD000111 (2002).

* cited by examiner

BIRTHING POOL MONITOR SYSTEM AND METHOD

CROSS-REFERENCE TO RELATED APPLICATIONS

This application is a U.S. National Phase Application of PCT/GB2020/050131, filed Jan. 21, 2020, which claims priority to GB 1900882.0, filed Jan. 22, 2019, the contents of which applications are incorporated herein by reference in their entireties for all purposes.

BACKGROUND OF THE INVENTION

This invention relates generally to monitoring of a birthing mother during labour. More specifically, although not exclusively, this invention relates to a birthing pool, method, and system for monitoring a birthing mother during labour.

Water birthing has become increasingly popular in recent years as the benefits of this practice have become more widely known. Trials have shown that use of birthing pools during the initial stage of labour reduces the need for epidural and spinal analgesia (see Cluett E R, Burns E. Immersion in water in labour and birth. Cochrane Database Syst Rev. 2009(2)). Furthermore, it was found that immersion during the second stage of labour resulted in the mother reporting a generally higher level of satisfaction with the experience of child birth. Water birthing has used standard baths but is now more commonly practiced in specially designed birthing pools comprising a tub, which is partially filled with water. These birthing pools are commonly located in hospitals, birth centres or midwifery units, and home births are also known.

Water birthing comprises a mother-to-be entering the tub of a birthing pool, for example when she has entered the first (or a later) stage of labour. The tub may be filled with water either prior or subsequent to her entry thereinto. Assistants such as healthcare professionals (for example, midwives), and/or birth partners, family members, generally assist the mother-to-be. These assistants are generally located outside of the tub.

The use of equipment to monitor the expectant mother and/or the unborn child during labour is known. Devices may be used to monitor the heartbeat of the mother and/or foetus and/or the contractions of the birthing mother as labour progresses. Many of these devices require the birthing mother and/or baby to wear the device. For example, electronic foetal monitoring (EFM) measures the baby's heartbeat and the pattern of contractions experienced by the birthing mother by placing a wired electronic sensor on the abdomen of the birthing mother, which is held is place using elastic belts. This can be uncomfortable and cumbersome for the birthing mother for movement during labour because it can inhibit free movement. Further, some of these "contact" devices are not suitable for use in water. Even if they are configured for water birth, the movement inhibition may at least partially negate one of the main perceived benefits of water births. Moreover, although some women find the presence of technology and surveillance during labour to be a comfort, other women seek to 'medicalise' the birth of their baby as little as possible, for example, by using and/or being aware of as few monitoring devices as possible.

OBJECTS AND SUMMARY OF THE INVENTION

It is therefore a first non-exclusive object of the invention to provide a means for monitoring a birthing mother as labour progresses, for example, whilst progressing through labour using a birthing pool. It is a further non-exclusive object of the invention to provide a means for monitoring the progress of labour of a birthing mother that avoids or reduces one or more of the perceived or actual issues of the prior art.

Accordingly, a first aspect of the invention provides a birthing pool, the pool comprising a base and a peripheral wall upstanding from the base, the pool further comprising at least one motion sensor, the motion sensor preferably being located adjacent the peripheral wall and/or on the base, and wherein the at least one motion sensor is configured or configurable to detect the movement of the birthing mother in the pool.

In embodiments, the motion sensor is operatively connected or connectable to a processing means, e.g. a processor, for processing data on the frequency and/or duration of one or more period(s) of stasis of the birthing mother, e.g. corresponding to one or more contractions.

A further aspect of the invention provides a birthing pool, the pool comprising a base and a peripheral wall upstanding from the base, the pool further comprising at least one motion sensor, the motion sensor preferably being located adjacent the peripheral wall and/or on the base, and wherein the at least one motion sensor is operatively connected or connectable to a processing means, e.g. a processor, for processing data on the frequency and/or duration of one or more period(s) of stasis of the birthing mother, e.g. corresponding to one or more contractions.

Advantageously, the at least one motion sensor(s) is configured to automatically detect the movement of the birthing mother over time.

In embodiments, the at least one motion sensor is configured or configurable to send data to a computer comprising a memory means, a processor, and a program. In embodiments, the computer is configured to receive data from the at least one motion sensor, to store the data on the memory means, and/or to process the data using the processor by implementing the program, and/or to output information concerning the movement of the birthing mother in the pool. In this way, the information concerning the movement of the birthing mother in the pool may be interpreted by the computer such that the output information guides clinical decisions.

We have found that the motions of a birthing mother change as stage 1 and/or stage 2 labour progresses. For example, a period of stasis may occur when the birthing mother experiences a contraction. The birthing pool of the invention is able to measure the motion of the mother using the at least one motion sensor. In this way, for example, the frequency of the contractions and/or the duration of the contraction may be monitored using data from the at least one motion sensor. Additionally or alternatively, the general movement of the birthing mother, e.g. the general movement of her arms, her legs, her torso, and so on, may be indicative of a certain stage of labour and/or indicative of progress through a certain stage (and/or stages) of labour, for example during early labour (dilation of cervix up to 3 cm), active labour (dilation of cervix up to 7 cm) and transition stage (dilation of cervix up to 10 cm) of the first stage of labour and/or during the second stage of labour (delivery of the baby) and or the third stage of labour (delivery of the placenta). The motion data collected by the motion sensor is able to provide information to a healthcare professional on the progress of the labour and/or whether and when intervention is required. For example, by remotely monitoring the periodicity and/or length of contractions the healthcare professional may be provided with sufficient information to determine the progress of labour.

By the term "birthing pool", we mean any pool that is suitable for use in water birth, e.g. an inflatable pool or a rigid tub. Preferably, the at least one motion sensor is retrofitted to and/or detachable from the birthing pool. In this way, the components of the birthing pool are more easily cleaned and/or replaced, and/or are less easily damaged. However, in embodiments, the at least one motion sensor may be mounted to, for example, removably or permanently mounted to the birthing pool, for example, permanent mounting to the birthing pool may occur during manufacture.

The at least one motion sensor may be mounted above the birthing pool or directly to, or in close proximity with the peripheral wall and/or the base of the birthing pool. The at least one motion sensor may be configured, operable or suitable for sensing the movement of a birthing mother as she moves within the birthing pool, e.g. over a specified or predetermined period of time, and/or continuously. Additionally or alternatively, the at least one motion sensor may be configured, operable or suitable for sensing the frequency and/or duration of one or more period(s) of stasis, e.g. that may indicate the occurrence of a contraction.

In embodiments, one or more markers, e.g. stickers and/or ink, may be applied to the body of the birthing mother. The marker may comprise e.g. a mark visible in visible light and/or UV light. The at least one motion sensors may be configured to configurable to determine the position of the birthing mother's body, e.g. temporally. The one or more markers are distinguished from the monitors of the prior art for placement in contact with the birthing mother. It is the intention of the present invention that the birthing mother has little or no awareness of the one or more markers because these will not impede movement and/or cause discomfort. In embodiments the markers may be placed on one or more limbs and/or at one or more joints, for example limb joints. The markers may be placed on the torso of the mother. For example, the front and/or back of the torso. Markers may be applied to the hands and/or feet.

Advantageously, the birthing pool according to the invention is able to monitor the movement of a birthing mother without having to apply monitors that are in contact with the birthing mother. We believe that, in many cases, remote monitoring is more physically comfortable for the birthing mother and leads to a birthing mother being less aware of the monitoring equipment being used.

The birthing pool may comprise two or more motion sensors, for example, three, four, five, or plural, e.g. n, motion sensors. In embodiments, one or more of the plural motion sensors (e.g. each) may be mounted above the birthing pool and/or mounted to the peripheral wall and/or to the base of a birthing pool. For example, the plural motion sensors may be mounted in a ring configuration. The plural motion sensors may be mounted around and/or adjacent the peripheral wall of the birthing pool. The plural motion sensors may be located at different heights, from the base, i.e. the floor, when the birthing pool is in use. The plural motion sensors may be located adjacent to the peripheral wall of the birthing pool at different distances, e.g. at different heights, from the base, i.e. the floor, when the birthing pool is in use. For example, at least one motion sensor may be located adjacent the peripheral wall at or near to the base, and/or at least one motion sensor may be located equidistant from the base and a top edge of the peripheral wall, and/or at least one motion sensor may be located adjacent the peripheral wall at or near the top edge, when the birthing pool is in use.

Additionally or alternatively, there may be one or more motion sensors mounted on or near to the base of the birthing pool. For example, plural motion sensors may be mounted equidistant from one another in a formation or configuration across the base of the birthing pool.

Advantageously, the more motion sensors there are, for example in different locations within or proximate the birthing pool, the more data points that can be obtained (for example, relating to leg motion, torso motion and so on). The use of plural motion sensors in plural positions allows for real-time capture of a birthing mother's movement. The data may be used to provide information that may be used to determine the progress of the birth and/or the health of the birthing mother and/or baby.

Additionally or alternatively, the data from the plural motion sensors may be used to provide information about periods of stasis (which may, for example, indicate or correspond to the occurrence of a contraction and/or to a period of distress) to monitor the progress of the birth. For example, as the birth progresses, the periods of the birthing mother's stasis (corresponding to contractions) may well increase and/or the period between them may well decrease.

The at least one motion sensor may comprise or be provided by one or more of a "visual" motion sensor, e.g. a camera(s) and/or a "non-visual" motion sensor, e.g. an ultrasound sensor.

The birthing pool may further comprise a liner, e.g. a disposable liner. In use, the liner is placed within the birthing pool to cover the base and the peripheral wall, and the birthing pool is filled with water. Advantageously, the provision of a liner prevents the base and the peripheral wall from coming into contact with water before, during, and after use.

The at least one motion sensor may be located in between the liner and the peripheral wall and/or the base of the birthing pool. This is suitable for "non-visual" motion sensors.

Advantageously, if the at least one motion sensor is a "non-visual" motion sensor then the liner prevents the at least one motion sensor from coming into contact with the water in the birthing pool. This mitigates against damage to the components of the apparatus and/or is more hygienic by preventing infection from cross-contamination, e.g. from multiple users. For embodiments comprising a liner, preferably at least one motion sensor is an ultrasound sensor. However, at least one motion sensor may also be provided as a camera, which may be adjacent the liner and located within the water.

In an embodiment, data or datasets relating to contraction duration and/or periodicity, and the progress of the birth, may be provided by a memory means and a computer software program, e.g. an app held on a computing device, for display of motion data, e.g. to determine the progress of the birth.

The birthing pool may further comprise or be operably connectable or connected to a processing means, e.g. a processor. The processing means may be usable to process received motion data from the motion sensors of the birthing pool using the or a computer program, for example, to interpret the motion data and to provide information about the progress of the birth and/or the perceived or actual health status of the birthing mother and/or foetus to the healthcare professional or other person, which may be used, for example, to inform decisions about the management of the birth.

For example, the processing means may be able to process received motion data from the at least one motion sensor on the movement of the birthing mother using the computer program. Said processed data may relate to, for example, the contraction duration and/or frequency and/or periodicity of the birthing mother. In embodiments, additionally or alternatively the processed data may relate to the general movement of the birthing mother over time, e.g. leg motion, arm motion, torso motion and so on. The motion data may be used to provide information which may be used to inform a healthcare professional about the progress of the birth, for example the data and/or information may be used to inform decisions such as medical interventions during labour. The motion data and/or information may be used to trigger an alarm, for example a remote or local alarm, for example an automated alarm.

For the avoidance of doubt, any of the features described herein apply equally to any aspect of the invention.

A further aspect of the invention provides a system for measuring the movement of a birthing mother, the system comprising:
  a) a birthing pool, the pool comprising a base and a peripheral wall upstanding from the base, the pool further comprising at least one motion sensor, the motion sensor preferably being located adjacent the peripheral wall and/or on the base, and wherein the at least one motion sensor is configured or configurable to detect the movement of the birthing mother in the pool;
  b) a processing means, e.g. a processor, operatively connected to the at least one motion sensor;
wherein the system is configured, during or after a measurement by the at least one motion sensor of movement of the birthing mother over a predetermined period of time, to process using the processing means, data on the frequency and/or duration of one or more period(s) of stasis of the birthing mother, e.g. corresponding to one or more contractions.

A further aspect of the invention provides a system for measuring the movement of a birthing mother in a birthing pool, the system comprising:
  a) a birthing pool, the pool comprising a base and a peripheral wall upstanding from the base, the pool further comprising at least one motion sensor, the motion sensor preferably being located adjacent the peripheral wall and/or on the base, and wherein the at least one motion sensor is configured or configurable to detect the movement of the birthing mother in the pool;
  b) a memory means on which is stored a database comprising data relating to a birthing mother's movement over a predetermined period of time and the progress of labour;
  c) a computer program; and
  d) a processing means, e.g. a processor, operatively connected to the at least one motion sensor and the memory means;
wherein the system is configured, during or after a measurement by the at least one motion sensor of movement of the birthing mother over a predetermined period of time, to determine the progress of the labour and/or the health status of the birthing mother, by comparing the data from the at least one motion sensor with the data within the database of the memory means, using the computer program and the processing means.

The at least one motion sensor may comprise or consist of one or more of a camera and/or an ultrasound sensor.

Advantageously, the system of the invention enables the progress of labour to be monitored by measuring the movement of the birthing mother. More advantageously, the system enables such measurements to be performed remotely from the birthing mother using remote motion sensors.

The movement data collected from the at least one motion sensor may be compared using the processing means, with data stored on the memory means, to provide information about the progress of the birth and/or the health status of the birthing mother, e.g. whether the labour is progressing well or whether the birthing mother is experiencing any difficulty that may require a medical intervention.

The or a database of the or a memory means may further comprise values for a 'regular' labour, e.g. according to a model or parametrical model for a 'regular' labour and/or from data recorded from births from the general population. The system may enable the healthcare professional to compare the movement data of the birthing mother with data stored within the database and/or enable decision making about the management of the labour going forward.

The system, e.g. the memory means may be capable of storing data, e.g. data from the first stage or stages of labour, for example stage 1 of labour, and/or data from post-initial stages of labour, for example stage 2 of labour. The system may enable the birthing mother and/or the healthcare professional to perform comparisons between the motion data of the birthing mother at different stages of the labour, e.g. during the first stage of labour, for example from the first and/or initial stage of labour to a time point later on from the first and/or initial stage of labour, for example, from stage 1 of labour to stage 2 of labour. The comparison of data between different stages of labour enables the healthcare professional and/or birthing assistant to monitor the progress of the labour and/or to make decisions, e.g. in respect of whether to perform an intervention.

In embodiments, the memory means may be capable of storing motion data from actual labours, e.g. motion data recorded throughout the birth of a baby during a study, for example a clinical study with the consent of the birthing mother. The processing means may be configured or configurable to add motion data to the database of the memory means (e.g. that motion data received from the at least one motion sensor) and/or to refine the motion data or the motion dataset stored in the database and/or on the memory means. Refinement of the motion data stored in the database may enable the system to better monitor and/or detect and/or correlate the movement of the birthing mother to a specific stage of labour. For example, refinement of the motion data stored in the database may enable the system to alert a healthcare professional and/or birthing assistant to the birthing mother entering a new stage of labour and/or requiring medical intervention. In this way, the system is able to "learn" in order to provide more accurate information to the healthcare professional and/or birthing assistant during the management of the labour.

The memory means may store data corresponding to an accumulation of data, for example, an accumulation of stasis events (to provide an accumulation period), for example over a certain period of time. The or an alarm signal may trigger when the accumulation period over a certain period of time exceeds a threshold value. This may indicate that contractions The system, e.g. the birthing pool, may further comprise a control means, e.g. a controller or a control unit.

The control means may be configured to receive, in use, from the at least one motion sensor, temporally spaced datasets and to compare the datasets to detect movement of the birthing mother within the birthing pool.

The control means may be configured to generate a signal, for example in response to data or datasets received from the at least one motion sensor or to a comparison of the data or datasets. The signal may be indicative of movement or a lack of movement of a birthing mother, for example within a predetermined time period and/or at one or more, e.g. a plurality of, predetermined times or time intervals. The control means may be configured to capture data or a dataset from the at least one motion sensor at predetermined time intervals, which are preferably regular or consistent time intervals. The predetermined time period may comprise or be measured in hours, minutes or seconds. The predetermined time intervals may comprise or be measured in minutes, seconds, tenths of a second, hundredths of a second or milliseconds.

At least one or each of the predetermined time period and/or the predetermined time intervals may be configurable or programmable or adjustable. In embodiments, the system comprises an input means or input, which may be operatively connected to the control means. The input or input means may be configured or operable to receive, in use, a desired time period and/or a desired time interval from a birthing mother or healthcare professional. The control means may be configured or operable to receive a desired time period and/or a desired time interval from the input or input means and to adjust the predetermined time period and/or the predetermined time interval to correspond or correspond substantially to the desired time period or the desired time interval, respectively. In embodiments, the same input or input means may be used to input both the desired time period and the desired time interval. In other embodiments, the monitoring birthing pool comprises a different input or input means for inputting each of the desired time period and the desired time interval.

Additionally or alternatively, the control means may be programmed or programmable, for example, to activate and/or control the at least one motion sensor.

The controller or control unit may comprise one or more dials for activating or deactivating the at least one motion sensor. In embodiments comprising more than one motion sensor, the controller or control unit may comprise one or more dials for selectively activating or deactivating one or more of the plural motion sensors. The control unit may interface with, for example, a computer software program held on the or a computing device, for example the or an app held on a mobile device, such as a computer, smart phone or tablet. The computer software program may be programmed to conduct a measurement of a parameter, e.g. the motion over a predetermined and/or specified period of time of the birthing mother.

The system, e.g. the control means, may further comprise an alert means, e.g. to alert the healthcare professional that the at least one motion sensor has been incorrectly located near, in or on the birthing pool, and/or that the system is unable to perform a motion measurement using the at least one motion sensor.

Additionally or alternatively, the alert means may be configured to alert a healthcare professional that the motion measurements recorded by the at least one motion sensor, e.g. the at least one motion sensor, are indicative of a stage of labour that may require intervention by the healthcare professional. For example, the alert means may be configured to alert a healthcare professional that the motion measurements recorded by the at least one motion sensor, e.g. the at least one motion sensor, are indicative of a specified frequency or duration of periods of stasis of the birthing mother (corresponding to contractions), and that for example, the birthing mother requires help and/or intervention, e.g. to progress through a stage a labour and/or to reach a further stage of labour.

The alert means may comprise an audible or visual alert means or device. The alert means may comprise an audible means, for example, for providing an audible alert or indication or statement or description, e.g. that the at least one motion sensor has been incorrectly located near, in or on the birthing pool. The alert means may comprise a display means or display, for example, for providing a visual representation, e.g. that the at least one motion sensor has been incorrectly located near, in, or on the birthing pool. The system may further comprise a data transfer means or element or module or component or device, for example a port, e.g. a USB or serial port, or a wireless transmitter, e.g. a radio or Bluetooth or Wifi transmitter, for transferring data from at least one of the memory means for review or analysis.

Additionally or alternatively, the system may comprise a display for displaying data stored in or on at least one of the memory means.

The system may further comprise a data transfer means or element or module or component or device, for example a port, e.g. a USB or serial port, or a wireless transmitter, e.g. a radio or Bluetooth or Wi-Fi transmitter, for transferring data from at least one of the memory means for review or analysis. Additionally or alternatively, the system may comprise a display for displaying data stored in or on at least one of the memory means.

The system may further comprise a communication means, e.g. for communicating with, for transmitting or transferring data to a remote server, e.g. an office of a doctor, for example, an obstetrician.

The communication means may comprise a communication element or module or component or device and/or may include a wireless communication or telecommunication means or system or a transmitter or wireless transmitter or receiver or a wireless receiver. Preferably, the communication means is operatively connected to the processing means. More preferably, the system is configured or programmed to cause the communication means to transmit, e.g. on or after detection of motion data, at least some of the data set, for example to a server or remote server.

The system may further comprise a server, e.g. a remote server, which may comprise a server communication means, e.g. for receiving data from the at least one motion sensor and/or for sending data to the at least one motion sensor. The server communication means may comprise a communication element or module or component or device and/or may include a wireless communication or telecommunication means or system or a transmitter or wireless transmitter or receiver or a wireless receiver.

A yet further aspect of the invention provides a method of monitoring the movement of a birthing mother, the method comprising providing a birthing pool comprising a base and a peripheral wall upstanding from the base, and locating at least one motion sensor adjacent the peripheral wall and/or on the base of the birthing pool, and detecting the movement of a birthing mother in the pool using the at least one motion sensor.

The motion sensor is remote from the mother. The method may further comprise comparing the data received from at least one motion sensor with a dataset, e.g. stored within a database on a memory means, to determine the frequency and/or duration of periods of stasis, for example, which correspond to contractions.

The method may further comprise providing an alert means for alerting a healthcare professional when a birthing mother experiences a specified frequency and/or duration of one or more periods of stasis, for example, corresponding to contractions.

Accordingly, the invention allows for the progress of labour and/or a stage of labour to be monitored remotely. The invention allows for the progress of labour and/or a stage of labour to be monitored in a non-contact fashion. The invention allows for the progress of labour and/or a stage of labour to be monitored and/or determined.

The above description specifies that the at least one motion sensor is located in or on the wall of the birthing pool. Alternatively or additionally the or a motion sensor may be located above the birthing pool, for example on a frame or other supporting structure.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. For the avoidance of doubt, the terms "may", "and/or", "e.g.", "for example" and any similar term as used herein should be interpreted as non-limiting such that any feature so-described need not be present. Indeed, any combination of optional features is expressly envisaged without departing from the scope of the invention, whether or not these are expressly claimed. The applicant reserves the right to change any originally filed claim or file any new claim accordingly, including the right to amend any originally filed claim to depend from and/or incorporate any feature of any other claim although not originally claimed in that manner.

BRIEF DESCRIPTION OF THE DRAWINGS

Embodiments of the invention will now be described by way of example only with reference to the accompanying drawings in which.

DESCRIPTION OF PREFERRED
EMBODIMENTS OF THE INVENTION

Figure 1:
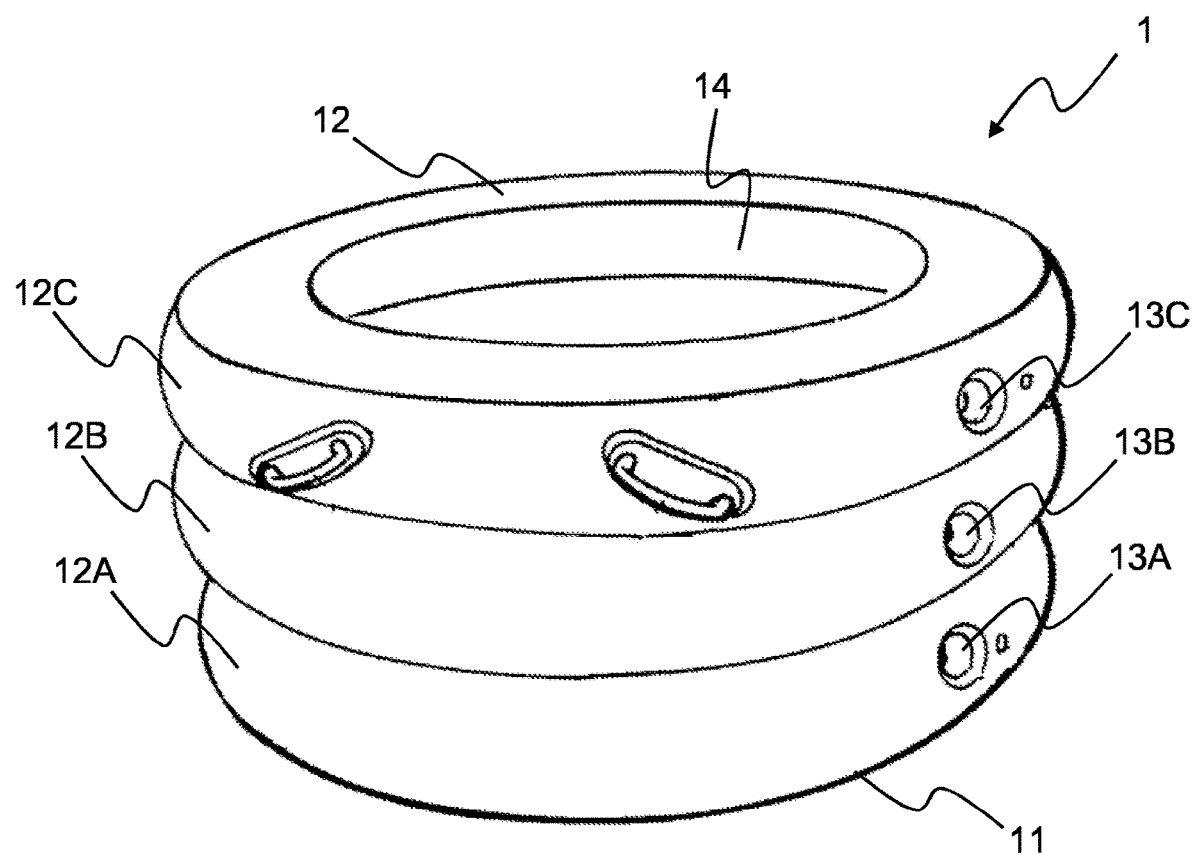
FIG. 1 is an inflatable birthing pool of the prior art.

Referring now to FIG. 1, there is shown an inflatable birthing pool 1 according to that disclosed in GB2432116. The inflatable birthing pool 1 comprises a base 11 and a peripheral wall 12. The peripheral wall 12 comprises three chambers; a first chamber 12A, a second chamber 12B, and a third chamber 12C. The peripheral wall 12 further comprises three valves; a first valve 13A in the first chamber 12A, a second valve 13B in the second chamber 12B, and a third valve 13C in the third chamber 12C. The inflatable birthing pool 1 further comprises a disposable liner 14.

In use, the inflatable birthing pool 1 is inflated by introducing air into each of the three chambers 12A, 12B, 12C through the three valves 13A, 13B, 13C respectively. The disposable liner 14 is arranged in the interior cavity created by inflation. The inflatable birthing pool 1 is then filled with water (not shown) such that the disposable liner 14 is in direct contact with the water only.

Figure 2:
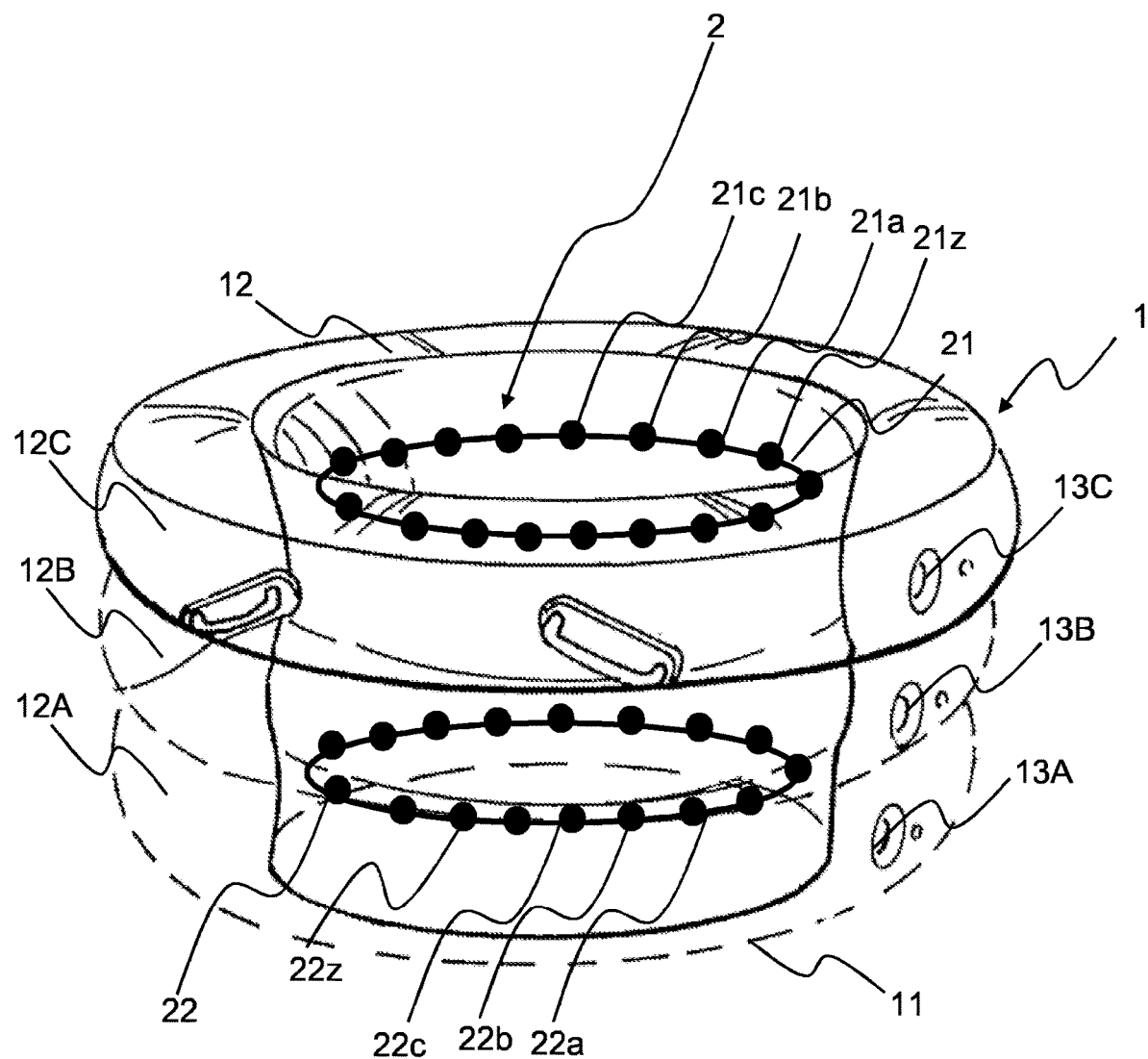
FIG. 2 is the inflatable birthing pool of FIG. 1 further comprising the monitoring birthing pool according to the first embodiment of the invention.

Referring now to FIG. 2, there is shown the inflatable birthing pool 1 of FIG. 1 further comprising a monitoring birthing pool 2 according to the first embodiment of the invention.

In this embodiment, the monitoring birthing pool 2 comprises a first series of motion sensors 21 and a second series of motion sensors 22. The first series of motion sensors 21 comprises plural motion sensors 21a, 21b, 21c . . . 21z although only some have been labelled in FIG. 2. Likewise, the second series of motion sensors 22 comprises plural motion sensors 22a, 22b, 22c . . . 22z.

The first and second series of motion sensors 21, 22 are each located as an annulus on the interior of the peripheral wall 12 of the inflatable birthing pool 1. The disposable liner 14 is then arranged to cover the first and second series of motion sensors 21, 22, in use.

Advantageously, this arrangement prevents the first and/or second series of motion sensors 21, 22 from becoming damaged by the water located in the disposable liner 14 of the inflatable birthing pool 1, when in use.

In use, the first and/or second series of motion sensors 21, 22 are able to sense the movement of a birthing mother, over a predetermined period of time, to determine periods of stasis. This data may be used to determine the frequency and/or duration of contractions. Such information may be used to inform decisions about the management of the birth.

Figure 3A:
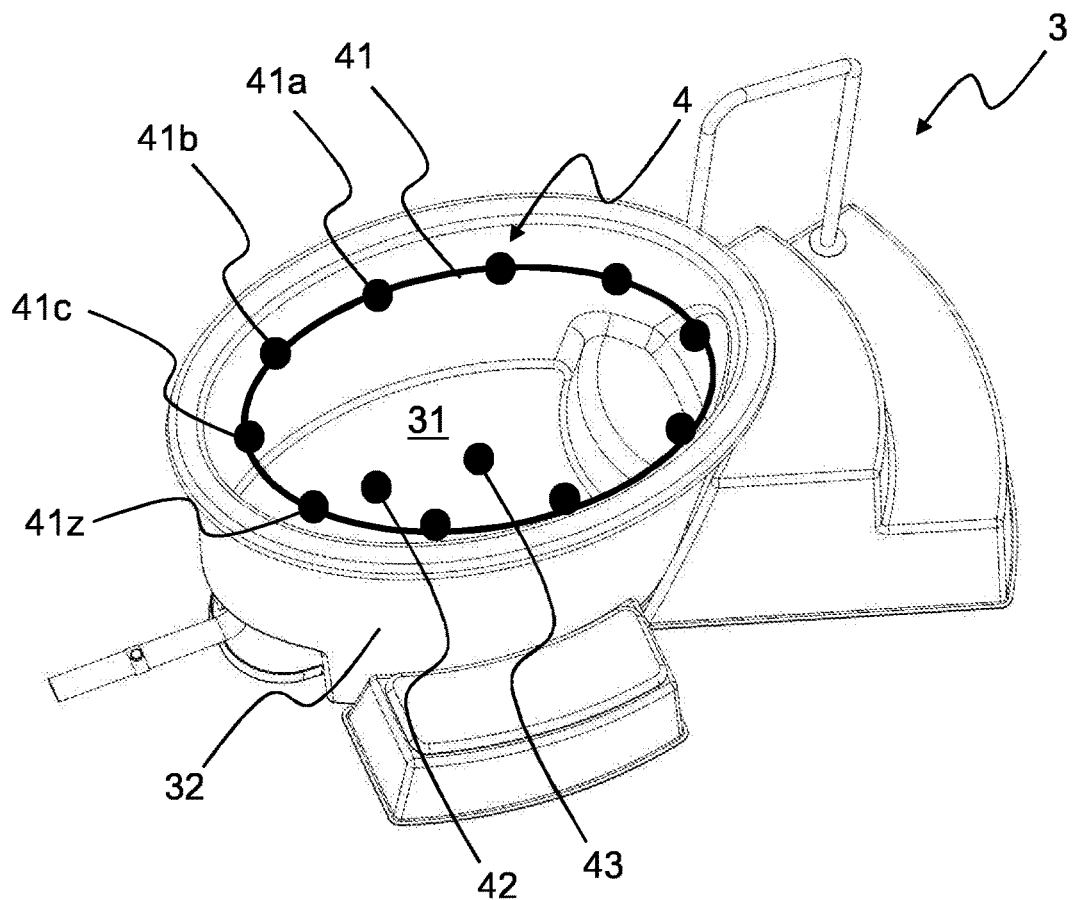
FIG. 3A is a rigid birthing pool comprising the monitoring birthing pool according to a second embodiment of the invention.
Figure 3B:
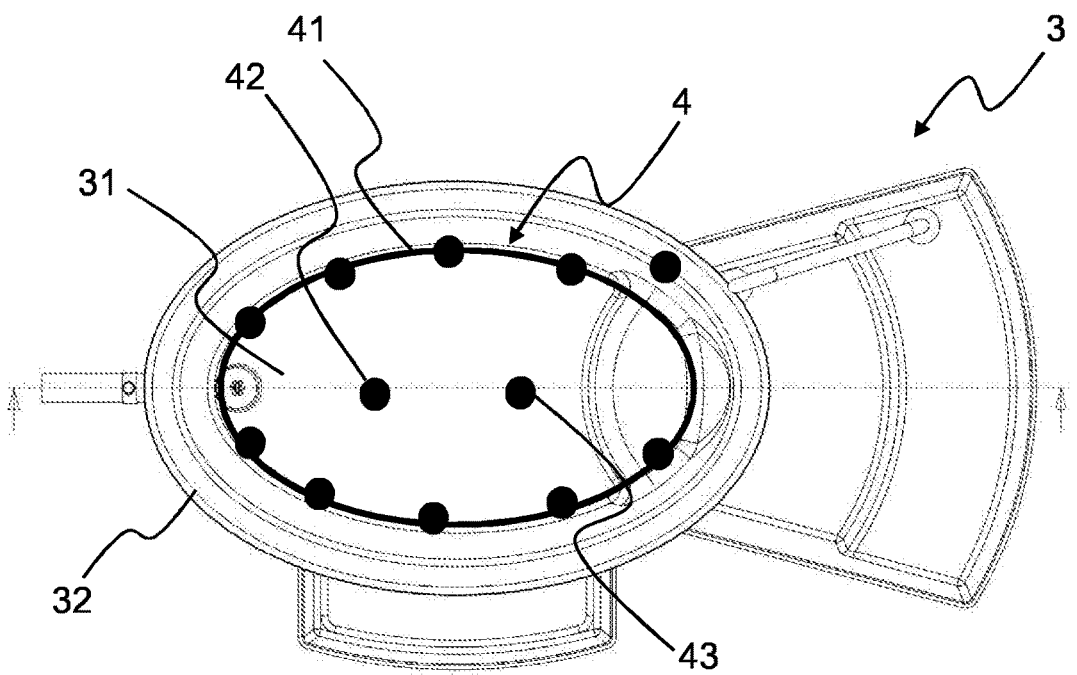
FIG. 3B is a rigid birthing pool comprising the monitoring birthing pool of FIG. 3A.

Referring now to both FIG. 3A and FIG. 3B, there is shown a rigid birthing pool 3 of the prior art. The rigid birthing pool 3 comprises a base 31 and a peripheral wall 32. The peripheral wall 32 is formed from a rigid material that does not require inflation to upstand from the base 31. In this embodiment, a disposable liner is not present, but may be used with the rigid birthing pool 3.

The rigid birthing pool 3 further comprises a monitoring birthing pool 4 according to the second embodiment of the invention.

In this embodiment, the monitoring birthing pool 4 comprises one series of motion sensors 41 only. However, a second, third or further series of motion sensors may be used if required with the rigid birthing pool in alternative embodiments. The series of motion sensors 41 comprises plural motion sensors 41a, 41b, 41c . . . 41z.

The series of motion sensors 41 is located as an annulus on the interior of the peripheral wall 32 of the rigid birthing pool 3.

The monitoring birthing pool 4 further comprises a first and a second motion single sensors 42, 43 located on the internal wall of the base 31 of the rigid birthing pool 3.

Advantageously, the more motion sensors there are in different locations within the rigid birthing pool 3, the more motion data points that can be obtained, e.g. relating to leg motion, torso motion and so on.

The motion sensors 41a, 41b, 41c . . . 41z, 42, 43 in this embodiment are waterproof such that, in use, these are not damaged when the rigid water bath 3 is filled with water.

In use, the series of motion sensors 41, together with the first and second single sensors 42, 43 are able to sense the movement of a birthing mother, over a predetermined period of time, to determine periods of stasis. This data may be used to determine the frequency and/or duration of contractions. Such information may be used to inform decisions about the management of the birth.

In either the first or second embodiment, markers may be applied to the body of the birthing mother to aid in motion detection. For example a mark may be applied to parts of the mother's body to facilitate motion capture or in-motion capture. The mark may comprise a sticker or an ink. The mark may be visible in visible light or may, for example be visible in a wavelength not in the visible wavelength range. The marks may comprise a substance that fluoresces or phosphoresces. The marks will be unobtrusive as possible. In one example one or more marks may be applied to the lower and upper legs and arms and the torso of the mother. The sensors may be arranged to monitor the movement of the marks and thereby determine the motion of the mother.

Figure 4:
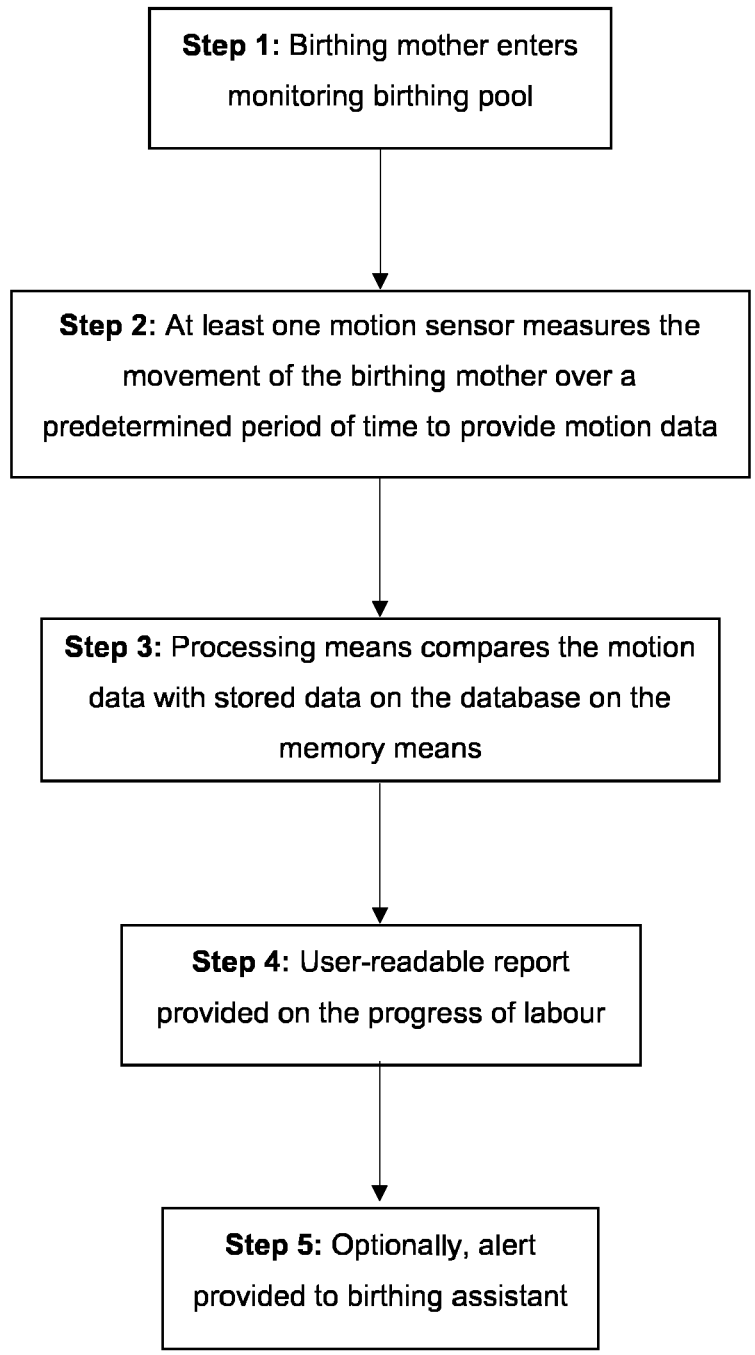
FIG. 4 is a flow diagram according to embodiments of a system of the invention.

Referring now to FIG. 4, there is shown a flow diagram 30 for a system according to embodiments of the invention.

In Step 1 of the system, the birthing mother enters the monitoring birthing pool comprising a least one motion sensor, e.g. the birthing pool of FIG. 2 or 3A, 3B.

In Step 2 of the system, the at least one motion sensor measures the movement of the birthing mother over a predetermined period of time, e.g. seconds or minutes, to collect motion data.

In Step 3 of the system, a processing means compares the motion data with stored data on a database of a memory means.

In Step 4, the processing means converts the comparison of the motion data with the stored data to provide a user-readable, e.g. birthing assistant-readable, report or read-out. The report may be presented on a display. The user-readable report may be a user-readable dataset to determine the progress of the labour and/or the health status of the birthing mother. Additionally or alternatively, the report may comprise phrases corresponding to the progress of the labour measured by the system.

In Step 5, the processing means, e.g. via a display means, provides an optional alert to the birthing assistant. The alert may comprise an alarm or a read-out. The alert may communicate to the birthing assistant that the birthing mother is entering a further stage of labour and/or that an intervention is required.

The motion sensor and associated processor may continuously monitor and interpret motion data during the course of the labour.

It will be appreciated by those skilled in the art that several variations to the aforementioned embodiments are envisaged without departing from the scope of the invention.

It will also be appreciated by those skilled in the art that any number of combinations of the aforementioned features and/or those shown in the appended drawings provide clear advantages over the prior art and are therefore within the scope of the invention described herein.

The invention claimed is:

1. A system for measuring the movement of a birthing mother in a birthing pool, the system comprising:
   a) The birthing pool, the pool comprising a base and a peripheral wall upstanding from the base, the pool further comprising at least one motion sensor, which is configured or configurable to detect the movement of the birthing mother in the pool and collect motion data;
   b) A processor operatively connected to the at least one motion sensor and usable to interpret the motion data and to provide information about the progress of the birth;
   wherein the system is configured to monitor motion of the mother whilst located within the birthing pool.

2. A system for measuring the movement of a birthing mother in a birthing pool, the system comprising:
   a) the birthing pool, the pool comprising a base and a peripheral wall upstanding from the base, the pool further comprising at least one motion sensor, which is configured or configurable to detect the movement of the birthing mother in the pool;
   b) a processor operatively connected to the at least one motion sensor;
   wherein the system is configured to monitor motion of the mother whilst located within the birthing pool and wherein the system is configured, during or after a measurement by the at least one motion sensor of movement of the birthing mother over a predetermined period of time, to process using processor, data on the frequency and/or duration of one or more period(s) of stasis of the birthing mother.

3. The system according to claim 1, further comprising a memory on which is stored a database for the conversion of the motion data from the birthing mother's movement over a predetermined period of time, into data on the progress of the labour.

4. The system according to claim 3, wherein the system is configured, during or after a measurement of movement of the birthing mother over a predetermined period of time, to determine the progress of the labour and/or the health status of the birthing mother, by comparing the motion data from the at least one motion sensor with the data within the database of the memory, using the processor.

5. A system for measuring the movement of a birthing mother in a birthing pool, the system comprising:
   a) the birthing pool, the pool comprising a base and a peripheral wall upstanding from the base, the pool further comprising at least one motion sensor, which is configured or configurable to detect the movement of the birthing mother in the pool;
   b) a processor operatively connected to the at least one motion sensor;
   wherein the system is configured to monitor motion of the mother whilst located within the birthing pool and further comprising a controller or a control unit, wherein the controller or the control unit is configured to generate a signal indicative of a specified and/or predetermined duration of a period of stasis of the birthing mother; and/or wherein the controller or the control unit is configured to generate a signal indicative of a specified and/or predetermined frequency of more than one periods of stasis of the birthing mother.

6. The system according to claim 1, further comprising an alert.

7. The system according to claim 6, wherein the alert is configured to alert a healthcare professional when the signal is generated.

8. The system according to claim 7, comprising an audible and/or a visual alert to the healthcare professional.

9. The system according to claim 1, further comprising a communicator.

10. The system according to claim 9, wherein the communicator is configured to communicate with, transmit and/or transfer data to a remote server.

11. A method of monitoring the movement of a birthing mother, the method comprising providing a birthing pool comprising a base and a peripheral wall upstanding from the base, and locating at least one motion sensor adjacent the peripheral wall and/or on the base of the birthing pool, and detecting the movement of a birthing mother in the pool using the at least one motion sensor, and collecting motion data using the at least one motion sensor and using a processing means operatively connected to the at least one motion sensor to interpret the motion data to provide information about the progress of the birth.

12. A method of monitoring the movement of a birthing mother, the method comprising providing a birthing pool comprising a base and a peripheral wall upstanding from the base, and locating at least one motion sensor adjacent the peripheral wall and/or on the base of the birthing pool, and detecting the movement of a birthing mother in the pool using the at least one motion sensor, the method further comprising comparing the data received from the at least one motion sensor with a dataset.

13. The method according to claim 11, further comprising providing an alert to alert a healthcare professional when a birthing mother experiences a specified frequency and/or duration of one or more periods of stasis.

14. A birthing pool, the pool comprising a base and a peripheral wall upstanding from the base, the pool further comprising at least one motion sensor, the motion sensor being located adjacent the peripheral wall and/or on the base, and wherein the at least one motion sensor is configured or configurable to detect the movement of the birthing mother in the pool, or wherein the at least one motion sensor is operatively connected or connectable to a processor for processing data on the frequency and/or duration of one or more period(s) of stasis of the birthing mother.

15. The birthing pool according to claim 14, comprising plural motion sensors, and wherein each of the plural motion sensors, comprises one of a camera or an ultrasound sensor.

16. The birthing pool according to claim 14, wherein the at least one motion sensor is detachable from the birthing pool, or wherein the at least one motion sensor is integrally formed with the birthing pool.

17. The birthing pool according to claim 14, further comprising a liner, and wherein the at least one motion sensor is located between the liner and the peripheral wall and/or base of the birthing pool.

18. The birthing pool according to claim 14, wherein the at least one motion sensor is configured, in use, to detect the duration and/or the frequency of one or more period(s) of stasis of a birthing mother.

19. The birthing pool according to claim 14, further comprising a computer program configured to process received movement data from the at least one motion sensor on the movement of the birthing mother and/or the birthing pool further comprising a controller or a control unit, wherein the controller or the control unit is programmed or programmable to activate and/or deactivate the at least one motion sensor.

20. A method according to claim 12, wherein the data is stored within a database on a memory and comparing said data received from the at least one motion sensor with the dataset allows a determination of the frequency and/or duration of periods of stasis.

\* \* \* \* \*